United States Patent [19]

Wain-Hobson et al.

[11] Patent Number: 5,019,510
[45] Date of Patent: May 28, 1991

[54] ISOLATION, MOLECULAR CLONING AND SEQUENCING OF AN HIV-1 ISOLATE FROM A GABONESE DONOR

[75] Inventors: Simon Wain-Hobson, Montigny le Bretonneux; Thierry Huet, Aubervilliers; Eric Delaporte; Francoise Brun-Vezinet, both of Paris, all of France

[73] Assignee: Institut Pasteur, Paris, France

[21] Appl. No.: 113,655

[22] Filed: Oct. 28, 1987

[51] Int. Cl.$^5$ .............................................. C12N 7/02
[52] U.S. Cl. .................................... 435/235.1; 435/5; 435/974; 435/239; 935/1; 935/3; 935/9
[58] Field of Search .......................... 435/235, 5, 172.1

[56] References Cited

U.S. PATENT DOCUMENTS 4,708,818  11/1987  Montagnier et al. ................... 435/5
4,752,565   6/1988  Folks et al. ........................ 435/236

OTHER PUBLICATIONS

Hahn et al., *PNAS* U.S.A. 82:4813–4817, 1985.

*Primary Examiner*—Richard A. Schwartz
*Assistant Examiner*—Johnny F. Railey, II
*Attorney, Agent, or Firm*—Finnegan, Henderson, Farabow, Garrett & Dunner

[57] ABSTRACT

A new strain of Human Immunodeficiency Virus (HIV), which is the major etiological agent of Acquired Immune Deficiency Syndrome (AIDS), is identified. The new strain, products derived from the new strain, a diagnostic method for detecting antibodies to the strain in biological fluids, and a diagnostic kit for carrying out the method are described.

7 Claims, 15 Drawing Sheets

```
          10        20        30        40        50
MGARASVLSGGELDKWEKIRLRPGGKKKYQLKHIVWASRELERFAINPGLLETSEGCRQI ←—HIV_OYI
::::::::::::::: :::::::::::::::: ::::::::::::::: ::::::::::
MGARASVLSGGELDRWEKIRLRPGGKKKYKLKHIVWASRELERFAVNPGLLETSEGCRQI ←—HIV_BRU
          10        20        30        40        50

70        80        90       100       110
LGQLQPSLKTGSEEIRSLYNTVATLYCVHQKIEVKDTKEALDKIEEEQNKSKKKAQQTAA
::::::::: :::::: :::::::::::::: :: :::::::::::::::::::::: ::
LGQLQPSLQTGSEELRSLYNTVATLYCVHQRIEIKDTKEALDKIEEEQNKSKKKAQQAAA
         70        80        90       100       110

130       140       150       160       170
DTGNSSQVSQNYPIVQNLQGQMVHQPISPRTLNAWVKVVEEKAFSPEVIPMFSALAEGAT
::: :::::::::::::: ::::::: ::::::::::::::::::::::::::::: :::
DTGHSSQVSQNYPIVQNIQGQMVHQAISPRTLNAWVKVVEEKAFSPEVIPMFSALSEGAT
       130       140       150       160       170

190       200       210       220       230
PQDLNTMLNTVGGHQAAMQMLKETINEEAAEWDRLHPVHAGPIAPGQMREPRGSDIAGTT
:::::::::::::::::::::::::::::::::::: :::::::::::::::::::::::
PQDLNTMLNTVGGHQAAMQMLKETINEEAAEWDRVHPVHAGPIAPGQMREPRGSDIAGTT
       190       200       210       220       230

250       260       270       280       290
STLQEQIGWMTNNPPIPVGEIYKRWIILGLNKIVRMYSPTSILDIRQGPKEPFRDYVDRF
::::::::::::::::::::::::::::::::::::::::::::::::::::::::::::
STLQEQIGWMTNNPPIPVGEIYKRWIILGLNKIVRMYSPTSILDIRQGPKEPFRDYVDRF
       250       260       270       280       290

310       320       330       340       350
YKTLRAEQASQDVPGWMTETLLVQNANPDCKIILKALGPAATLEEMMTACQGVGGPGHKA
:::::::::::: : ::::::::::::::::: :::::::::::::::::::::::::::
YKTLRAEQASQEVKNWMTETLLVQNANPDCKTILKALGPAATLEEMMTACQGVGGPGHKA
       310       320       330       340       350

370       380       390       400       410
RVLAEAMSQV-NSVTVMMQKGNFKNQRKTVKCFNCGKEGHIAKNCRAPRKKGCWKCGREG
::::::::::  ::  :::::::: ::: ::::::::::::: ::::::::::::::: :
RVLAEAMSQVTNSATIMMQRGNFRNQRKIVKCFNCGKEGHIARNCRAPRKKGCWKCGKEG
       370       380       390       400       410

420       430       440              450       460
HQMKDCTERQANFLGKIWPSHKGQGN------------FLQNRPEPTAPPAESFGFGEE
::::::::::::::::::::: :::::            ::.::::::::: :::  ::
HQMKDCTERQANFLGKIWPSYKGRPGNFLQSRPEPTAPPFLQSRPEPTAPPEESFRSGVE
          430       440       450       460       470

470       480       490
TTTPPQKQEPIDKGLYPLTSLRSLFGNDPSSQ
::::  :::::::: :::::::::::::::::
TTTPSQKQEPIDKELYPLTSLRSLFGNDPSSQ
     490       500       510
```

FIG. 1

```
       10                    20        30         40
FFREDLAFPQGTGE-------------FSSEQTRANSPTSRELRVWGRDNNSPSEAGADR ←—HIV_OYI
::::::::::: ::              ::::::::::::: ::: ::::::: :::::::
FFREDLAFLQGKAREFSSEQTRANSPTFSSEQTRANSPTRRELQVWGRDNNSLSEAGADR ←—HIV_BRU
       10        20        30        40        50

50        60        70        80        90       100
QGTVSFNLPQITLWQRPIVTIKIGGQLKEALLDTGADDTVLEEMNLPGRWKPKMIGGIGG
:::::: :::::::::: :::::::::::::::::::::::::: ::::::::::::::
QGTVSFNFPQITLWQRPLVTIKIGGQLKEALLDTGADDTVLEEMSLPGRWKPKMIGGIGG
       70        80        90       100       110

110       120       130       140       150       160
FIKVRQYDQILIEICGHKAIGTVLVGPTPVNIIGRNLLTQLGCTLNFPISPIETVPVKLK
:::::::::::::::::::::::::::::::::::::::: :::::::::::::::::::
FIKVRQYDQILIEICGHKAIGTVLVGPTPVNIIGRNLLTQIGCTLNFPISPIETVPVKLK
      130       140       150       160       170

170       180       190       200       210       220
PGMDGPKVKQWPLTEEKIKVLIEICTEMEKEGKISKVGPENPYNTPVFAIKKKDSTKWRK
::::::::::::::::::::: ::::::::::::::: :::::::::::::::::::::
PGMDGPKVKQWPLTEEKIKALVEICTEMEKEGKISKIGPENPYNTPVFAIKKKDSTKWRK
      190       200       210       220       230

230       240       250       260       270       280
LVDFRELNKRTQDFWEAQLGIPHPAGLKKKKSVTVLDVGDAYFSVPLDKDFRKYTAFTIP
::::::::::::::::: :::::::::::::::::::::::::::::::: :::::::::
LVDFRELNKRTQDFWEVQLGIPHPAGLKKKKSVTVLDVGDAYFSVPLDEDFRKYTAFTIP
      250       260       270       280       290

290       300       310       320       330       340
SINNETPGLRYQYNVLPQGW-GSPAIFQSSMTKILEPFRKQNPDIVIYQYMDDLYVGSDL
:::::::: ::::::::::: ::::::::::::::::::::::::::::::::::::::
SINNETPGIRYQYNVLPQGWKGSPAIFQSSMTKILEPFRKQNPDIVIYQYMDDLYVGSDL
      310       320       330       340       350

350       360       370       380       390       400
EIGQHRTKIEELRQHLLRWGFTTPDKKHQKEPPFLWMGYELHPDKWTVQPIMLPEKDSWT
::::::::::::::::::::: ::::::::::::::::::::::::::::::: :::::
EIGQHRTKIEELRQHLLRWGLTTPDKKHQKEPPFLWMGYELHPDKWTVQPIVLPEKDSWT
      370       380       390       400       410

410       420       430       440       450       460
VNDIQKLVGKLNWASQIYAGIKVKNLCKLLRGTKALTEVIPLTEEAELELAENREILKEP
::::::::::::::::::: :::::: :::::::::::::::::::::::::::::::::
VNDIQKLVGKLNWASQIYPGIKVRQLCKLLRGTKALTEVIPLTEEAELELAENREILKEP
      430       440       450       460       470

470       480       490       500       510       520
VHG-YYDPSKDLVAELQKQGQGQWTYQIYQEPFKNLKTGKYARMRGAHTNDVKQLTEAVQ
::: :::::::: ::::::::::::::::::::::::::::::: :::::::::::::::
VHGVYYDPSKDLIAEIQKQGQGQWTYQIYQEPFKNLKTGKYARTRGAHTNDVKQLTEAVQ
      490       500       510       520       530
```

FIG. 2-1

```
530        540        550        560        570        580
KITQDRIVIWGKTPKFKLPIQKETWEAWWTEYWQATWIPEWEFVNTPPLVKLWYQLEKDP
::: ::::: ::::::::::::::::::: ::::::::::::::::::::::::::: :
KITTESIVIWGKTPKFKLPIQKETWERWWTEYWQATWIPEWEFVNTPPLVKLWYQLEKEP
      550        560        570        580        590

590        600        610        620        630        640
IVGAETFYVDGAANRETKLGKAGYVTDRGRQKVVSLTDTTNQKTELQAIHLALQDSGLEV
::::::::::: :::::::::::::: :::::: ::::::::::::::::::::::::::
IVGAETFYVDGAASRETKLGKAGYVTNRGRQKVVTLTDTTNQKTELQAIHLALQDSGLEV
      610        620        630        640        650

650        660        670        680        690        700
NIVTDSQYALGIIQAQPDKSESELVSQIIEQLIKKEKVYLAWVPAHKGIGGNEQVDKLVS
:::::::::::::::::::::::::: :::::::::::::::::::::::::::::::::
NIVTDSQYALGIIQAQPDKSESELVNQIIEQLIKKEKVYLAWVPAHKGIGGNEQVDKLVS
      670        680        690        700        710

710        720        730        740        750        760
AGIRKVLFLDGIDKAQEEHEKYHSNWRAMASDFNLPPVVAKEIVASCDKCQLKGEAMHGQ
::::::::::::::::: ::::::::::::::::::::::::::::::::::::::::::
AGIRKVLFLDGIDKAQDEHEKYHSNWRAMASDFNLPPVVAKEIVASCDKCQLKGEAMHGQ
      730        740        750        760        770

770        780        790        800        810        820
VDCSPGIWQLDCTHLEGKIILVAVHVASGYIEAEVIPAETGQETAYFILKLAGRWPVKTI
:::::::::::::::::: :::::::::::::::::::::::::::::: ::::::::::
VDCSPGIWQLDCTHLEGKVILVAVHVASGYIEAEVIPAETGQETAYFLLKLAGRWPVKTI
      790        800        810        820        830

830        840        850        860        870        880
HTDNGSNFTSTTVKAACWWAGIKQEFGIPYNPQSQGVVESMNNELKKIIGHVRDQAEHLK
:::::::::::::::::::::::::::::::::::::::::: ::::::: :::::::::
HTDNGSNFTSTTVKAACWWAGIKQEFGIPYNPQSQGVVESMNKELKKIIGQVRDQAEHLK
      850        860        870        880        890

890        900        910        920        930        940
TAVQMAVFIHNFKRKGGIGGYSAGERIVDIIATDIQTKELQKQITKIQNFRVYYRDSREP
:::::::::::::::::::::::::::::::::::::::::::::::::::::::::: :
TAVQMAVFIHNFKRKGGIGGYSAGERIVDIIATDIQTKELQKQITKIQNFRVYYRDSRDP
      910        920        930        940        950

950        960        970        980        990        1000
LWKGPAKLLWKGEGAVVIQDNSDIKVVPRRKAKIIRDYGKQMAGDDCVASRQDED
::::::::::::::::::::::::::::::::::::::::::::::::::::::
LWKGPAKLLWKGEGAVVIQDNSDIKVVPRRKAKIIRDYGKQMAGDDCVASRQDED
      970        980        990       1000       1010
```

FIG. 2-2

```
                10         20         30         40         50
      MENRWQVMIVWQVDRMRIRTWKSLVKHHMYVSKKAKGWFYRHHYESTHPRISSEVHIPLG ←HIV_OYI
      ::::::::::::::::::::::::::::::: :::.::::::::::: ::::::::::
      MENRWQVMIVWQVDRMRIRTWKSLVKHHMYVSGKARGWFYRHHYESPHPRISSEVHIPLG ←HIV_BRU
                10         20         30         40         50

70         80         90        100        110
      DATLVVTTYWGLHTGEREWHLGQGASIEWRKKRYSTQVDPGLADQLIHTYYFDCFSESAI
      :: ::.:::::::::::.:::::..:::::::::::::::.::::::.::::::..:::
      DARLVITTYWGLHTGERDWHLGQGVSIEWRKKRYSTQVDPELADQLIHLYYFDCFSDSAI
                70         80         90        100        110

130        140        150        160        170
      RNAILGNIVSPRCEYPAGHNKLGSLQYLALAALIKPKKIKPPLPSVTKLTEDRWNKPQKT
      :.:.::.:::::::::.:::::.::::::::::: :::::::::::::::::::::::
      RKALLGHIVSPRCEYQAGHNKVGSLQYLALAALITPKKIKPPLPSVTKLTEDRWNKPQKT
              130        140        150        160        170

190
      KGHRGSHTMNGH
      ::::::::::::
      KGHRGSHTMNGH                                  FIG. 3
              190

10         20         30         40         50
      MEQAPEDQGPQREPYNEWTLELLEELKSEAIRHFPRIWLHSLEQYIYETYGDTWEGVEAI ←HIV_OYI
      :::::::::::::: :::::::::::::.::.:::::::: : ::::::::::.::::
      MEQAPEDQGPQREPHNEWTLELLEELKNEAVRHFPRIWLHGLGQHIYETYGDTWAGVEAI ←HIV_BRU
                10         20         30         40         50

70         80         90
      IRMLQQLLFIHFRIGCQHSRIGITRQRRARNGASRS
      ::.::::::::::::::.:::::.::::::::::::              FIG. 4
      IRILQQLLFIHFRIGCRHSRIGVTQQRRARNGASRS
                70         80         90

10         20         30         40         50
      MEPVDPRLEPWKHPGSQPKTASNNCYCKRCCLHCQVCFTKKGLGISYGRKKRRQRRRAPQ ←HIV_OYI
      :::::::::::::::::::::: . ::::.:: ::::::::.:::::::::::::: ::
      MEPVDPRLEPWKHPGSQPKTACTTCYCKKCCFHCQVCFTTKALGISYGRKKRRQRRRPPQ ←HIV_BRU
                10         20         30         40         50

70         80         90        100
      DSKTHQVSLSKQPASQPRGDPTGPKESKKKVERETETDPED
        .:::::::::::.:::::::::::                       FIG. 5
      GSQTHQVSLSKQPTSPQRGDPTGPKE
                70         80

10         20         30         40         50
      MAGRSGDSDEELLKTVRLIKFLYQSNPPPNPEGTRQARRNRRRRWRERQRQIRKISGWIL ←HIV_OYI
      ::::::::::: ::.:::::::::::::::::::::::::::::::::::::. : :::
      MAGRSGDSDEDLLKAVRLIKFLYQSNPPPNPEGTRQARRNRRRRWRERQRQIHSISERIL
                10         20         30         40         50

70         80         90        100        110
      STYLGRSAEPVPLQLPPLERLNLDCSEDCGTSGTQGVGSPEILVESPAVLEPGTKE
      ::::::::::::::::::::::.:::.:::::::::::::.::::::.:::::::
      STYLGRSAEPVPLQLPPLERLTLDCNEDCGTSGTQGVGSPQILVESPTVLESGTKE       FIG. 6
                70         80         90        100        110
```

```
         10         20         30         40         50
MTARGTRKNYQRLWRWG----TMLLGMLMICSAAENLWVTVYYGVPVWKEATTTLFCASD   HIV_OYI
 : : :  :  ::::: ::   :::: ::::::::: : ::::::::::::::::::::
MRVKEKYQHLWRWGKWGTMLLGILMICSATEKLWVTVYYGVPVWKEATTTLFCASD      HIV_BRU
         10         20         30         40         50

60         70         80         90        100        110
ARAYATEVHNVWATHACVPTDPNPQEVVLGNVTENFDMWKNNMVEQMQEDIISLWDQSLK
 :Δ:  :::::::::::::::::::::: ::::::: :::::::::: :::::::::::
AKAYDTEVHNVWATHACVPTDPNPQEVVLVNVTENFNMWKNDMVEQMHEDIISLWDQSLK
         60         70         80         90        100        110

120        130        140        150        160
PCVKLTPLCVTLDCTDVNTTSSSLRNATNTTSSSWET------MEKGELKNCSFNTTTSI
::::::::::  ::::        :::::: ::::        :::::::::: : ::
PCVKLTPLCVSLKCTD-------LGNATNTNSSNTNSSSGEMMMEKGEIKNCSFNISTSI
        120        130        140        150        160

180        190        200        210        220
RDKMQEQYALFYKLDVLPIDKNDTKFRLIHCNTSTITQACPKISFEPIPMLYYCTPAGFA
: : ::: : ::::: :::::: ::: : :::: :::::::: ::::::: ::::::
RGKVQKEYAFFYKLDIIPIDNDTTSYTLTSCNTSVITQACPKVSFEPIPIHY-CAPAGFA
        180        190        200        210        220

240        250        260        270        280
ILKCNDKKFNGTPCTNVSTVQCTHGIKPVVSTQLLLNGSLAEEEVIIRSSNFTNNAKII
:::::::::::::::::::::::::: ::::::::::::::::::::::::: ::: ::
ILKCNNKTFNGTGPCTNVSTVQCTHGIRPVVSTQLLLNGSLAEEEVVIRSANFTDNAKTI
        230        240        250        260        270        280

300        310        320        330        340
IVQLNKSVEINCTRPNNNTRNRISI--GPGRAFHTTKQIIGDIRQAHCNLSRATWEKTLE
::::::::::::::::::::::::   :::::::  ::  : ::::::: ::::: :::
IVQLNQSVEINCTRPNNNTRKSIRIQRGPGRAFVTIGKI-GNMRQAHCNISRAKWNATLK
        290        300        310        320        330        340

350        360        370        380        390        400
QIATKLRKQFRN-KTIAFDRSSGGDPEIVMHSFNCGGEFFYCNTSQLFNSTWNDTTRA--
:::::::::::  ::::::::::::::::::::::::::::::::::::::::::::
QIASKLREQFGNNKTIIFKQSSGGDPEIVTHSFNCGGEFFYCNSTQLFNSTWFNSTWSTE
        350        360        370        380        390        400

410        420        430        440        450
--NSTEV--TITLPCRIKQIVNMWQEVGKAMYAPPISGQIRCSSKITGLLLTRDGGKNTT
  :: :   :::::::::::::::::::::::::::::::::: :::::::::::::
GSNNTEGSDTITLPCRIKQFINMWQEVGKAMYAPPISGQIRCSSNITGLLLTRDGGNNN-
        410        420        430        440        450        460

470        480        490        500        510
NGIEIFRPAGGDMRDNWRSELYKYKVVKIEPLGVAPTKARRRVVQREKRAVGMLGAMFLG
:: ::::::::::::::::::::::::::::::::: : ::::::::::::: ::::::
NGSEIFRPGGGDMRDNWRSELYKYKVVKIEPLGVAPTKAKRRVVQREKRAVGI-GALFLG
        470        480        490        500        510        520
```

FIG 7-1

```
          530       540       550       560       570
FLGAAGSTMGARSMTVTVQARQLLSGIVQQQNNLLRAIEAQQHLLQLTVWGIKQLQARVL
::::::::::::::: :::::::::::::::::::::::::::::::::::::::::::
FLGAAGSTMGARSMTLTVQARQLLSGIVQQQNNLLRAIEAQQHLLQLTVWGIKQLQARIL
          530       540       550       560       570       580

590       600       610       620       630
AVERYLKDQQLLGIWGCSGKLICTTTVPWNASWSNKSLNEIWDNMTWMQWEREIDNYTHL
:::::::::::::::::::::::: ::::::::::::: :::::::: ::::::::: :
AVERYLKDQQLLGIWGCSGKLICTTAVPWNASWSNKSLEQIWNNMTWMEWDREINNYTSL
          590       600       610       620       630       640

650       660       670       680       690
IYTLIEESQNQQEKNEQELLELDKWAGLWSWFSITNWLWYIGIFIIIIVGGLVGLRIVFA
  :::::::::::::::::::::::::: :::: :::::: :: : :  :::::::::::
IHSLIEESQNQQEKNEQELLELDKWASLWNWFNITNWLWYIKIFIMI-VGGLVGLRIVFA
          650       660       670       680       690       700

710       720       730       740       750
VLSIVNRVRQGYSPLSFQTRLPTQRGPDRPEGIEEEGGERDRDRSGRLVDGFLALIWDDL
::::::::::::::::::: ::::::::::::::::::::::::::: :::: ::::::
VLSIVNRVRQGYSPLSFQTHLPTPRGPDRPEGIEEEGGERDRDRSIRLVNGSLALIWDDL
          710       720       730       740       750       760

770       780       790       800       810
RSLCLFSYHRLRDLILIVARIVELLGRRGWEVLKYWWNLLQYWSQELKNSVISLLNATAI
:::::::::::::: :::: :::::::::::: ::::::::::::::::: :::::::::
RSLCLFSYHRLRDLLLIVTRIVELLGRRGWEALKYWWNLLQYWSQELKNSAVSLLNATAI
          770       780       790       800       810       820

830       840       850
AVAEGTDRVIEIVQRAYRAFLNIPRRIRQGLERALL
::::::::::: ::: : : ::::::::::::: ::
AVAEGTDRVIEVVQGACRAIRHIPRRIRQGLERILL
          830       840       850       860
```

FIG. 7-2

```
            10        20        30        40        50
MGGKWSKCSMKGWPTIRERMKRAELQPPEPAAEGVGAASRDLEKHGAITSSNTAATNADC←—HIV_OYI
::::::::::: :::: ::::   :: : :::: :::::::::::::::::::::: :
MGGKWSKSSVVGWPTVRERMR————RA—EPAADGVGAASRDLEKHGAITSSNTAATNAAC←—HIV_BRU
            10        20            30        40        50

70        80        90       100       110
AWLEAQEDEEVGFPVRPQVPLRPMTYKGALDLSHFLKEKGGLEGLIYSQKRQDILDLWVY
::::::: ::::::: :::::::::::   :::::::::::::::: :: :::::::::
AWLEAQEEEEVGFPVTPQVPLRPMTYKAAVDLSHFLKEKGGLEGLIHSQRRQDILDLWIY
    60        70        80        90       100       110

130       140       150       160       170
HTQGYFPDWQNYTPGPGIRYPLCFGWCFKLVPMDPDQVEEANEGENNSLLHPISLHGMDD
::::::::::::::::: :::: :::: ::::: :: ::::: ::: ::::: :::::
HTQGYFPDWQNYTPGPGVRYPLTFGWCYKLVPVEPDKVEEANKGENTSLLHPVSLHGMDD
    120       130       140       150       160       170

190       200      210
PEKEVLVWKFDSRLAFRHMAREVHPEYYKDC
:: ::: : :::::::: : :::: ::: :
PEREVLEWRFDSRLAFHHVARELHPEYFKNC
    180       190       200       210
```

FIG. 8

```
GGTCTCTCTAGCTAGACCAGATCTGAGCCCGGGAGCTCTCTGGCTAACTAGGGAACCCAC
TGCTTAAGCCTCAATAAAGCTTGCCTTGAGTGCTTCAAGTAGTGTGTGCCCGTCTGTTGT
GTGACTCTGGTAACTAGAGATCCCTCAGACCCTTTTAGTCAGTGTGGAAAATCTCTAGCA
GTGGCGCCCGAACAGGACCTTAAAGTGAAAGTGGAACCAGAGGAGCTCTCTCGACGCAGG
ACTCGGCTTGCTTAGCGCGCACGGCAAGAGGCGAGGGGCGGCGACTGGTGAGTACGCCAA
AAATTTTTGACTAGCGGAGGCTAGAAGGAGAGAGATGGGTGCGAGAGCGTCAGTATTAAG
CGGGGGAGAATTAGATAAATGCGAAAAAATTCGGTTAAGGCCAGGGGGAAAGAAAAAATA
TCAACTAAAACATATAGTATGGGCAAGCAGGGAGCTAGAACGATTCGCAATTAATCCTGG
CCTGTTAGAAACATCAGAAGGTTGTAGACAAATACTGGGACAGCTACAACCATCCCTTAA
GACAGGATCAGAAGAAATTAGATCATTATATAATACAGTAGCAACTCTTTATTGTGTGCA
TCAAAAGATAGAGGTAAAAGACACCAAGGAAGCTTTAGATAAGATAGAGGAAGAGCAAAA
CAAAAGTAAGAAAAAAGCACAGCAAACAGCAGCTGACACAGGAAACAGCAGCCAGGTCAG
CCAAAATTACCCTATAGTACAGAACCTTCAGGGGCAAATGGTACATCAGCCCATATCACC
TAGAACTTTAAATGCATGGGTAAAAGTAGTAGAAGAGAAGGCTTTCAGCCCAGAAGTAAT
ACCCATGTTTTCAGCATTAGCAGAAGGAGCCACCCCACAAGATCTAAACACCATGCTAAA
CACAGTGGGGGGACATCAAGCAGCCATGCAAATGTTAAAAGAGACCATCAATGAGGAAGC
TGCAGAATGGGATAGATTGCATCCAGTACATGCAGGGCCTATTGCACCAGGCCAGATGAG
AGAACCAAGGGGAAGTGACATAGCAGGAACTACTAGTACCCTTCAGGAACAAATAGGATG
GATGACAAATAATCCACCTATCCCAGTAGGAGAAATCTATAAAAGATGGATAATCCTGGG
ATTAAATAAAATAGTAAGAATGTATAGCCCTACCAGCATTCTGGACATAAGACAAGGACC
AAAGGAACCCTTTAGAGACTATGTAGACCGGTTCTATAAAACTCTAAGAGCCGAAGCAAGC
TTCACAGGATGTACCTGGTTGGATGACAGAAACCTTGTTGGTCCAAAATGCAAACCCAGA
TTGTAAGATCATTTTAAAAGCATTGGGACCAGCAGCTACACTAGAAGAAATGATGACAGC
ATGTCAGGGAGTGGGGGGACCCGGCCATAAAGCAAGAGTTTTGGCTGAAGCAATGAGCCA
AGTAAATTCAGTCACCGTAATGATGCAGAAAGGCAATTTTAAGAACCAAAGAAAGACTGT
TAAGTGTTTCAATTGTGGCAAAGAAGGGCACATAGCCAAAAATTGCAGGGCTCCTAGGAA
AAAGGGCTGTTGGAAATGTGGAAGGGAAGGACACCAAATGAAAGATTGTACTGAGAGACA
GGCTAATTTTTTAGGGAAGATCTGGCCTTCCCACAAGGGACAGGGGAATTTTCTTCAGAA
CAGACCAGAGCCAACAGCCCCACCAGCAGAGAGCTTCGGGTTTGGGGAAGAGACAACAAC
TCCCCCTCAGAAGCAGGAGCCGATAGACAAGGGACTGTATCCTTTAACCTCCCTCAGATC
ACTCTTTGGCAACGACCCATCGTCACAATAAAGATAGGGGGCAACTAAAAGAAGCTCTA
TTAGATACAGGAGCAGATGATACAGTATTAGAAGAAATGAATTTGCCAGGAAGATGGAAA
CCAAAAATGATAGGGGGAATTGGAGGTTTTATCAAAGTAAGACAGTATGATCAGATACTC
ATAGAAATCTGTGGACATAAAGCTATAGGTACAGTATTAGTAGGACCTACACCTGTCAAC
ATAATTGGAAGAAATCTGTTGACTCAGCTTGGTTGTACTTTAAATTTTCCCATTAGTCCT
ATTGAAACTGTACCAGTAAAATTAAAGCCAGGAATGGATGGCCCAAAAGTTAAACAATGG
CCATTGACAGAAGAGAAAATAAAAGTATTAATAGAAATTTGTACAGAAATGGAAAAGGAA
GGGAAAATTTCAAAAGTTGGGCCTGAAAATCCATACAATACTCCAGTATTTGCCATAAAG
AAAAAAGACAGTACTAAATGGAGAAAATTAGTAGATTTCAGAGAACTTAATAAGAGAACT
CAGGACTTCTGGGAAGCTCAATTAGGAATACCACATCCAGCAGGGTTAAAAAAGAAAAAA
TCAGTAACAGTACTGGATGTGGGTGATGCATACTTTTCAGTTCCCTTAGATAAAGACTTC
AGAAAGTATACTGCATTTACCATACCTAGTATAAACAATGAGACACCAGGGCTTAGATAT
CAGTACAATGTGCTTCCACAGGGATGG55AGGATCACCAGCGATATTCCAAAGTAGTATG
ACAAAAATCTTAGAGCCTTTTAGAAAACAAAATCCAGACATAGTTATCTATCAATACATG
GATGATTTGTATGTAGGATCTGACTTAGAAATAGGGCAGCATAGAACAAAAATAGAGGAA
CTGAGACAACATCTGTTGAGGTGGGGATTTACCACACCAGACAAAAAACATCAGAAAGAA
CCTCCATTCCTTTGGATGGGTTATGAACTCCATCCTGATAAATGGACAGTACAGCCTATA
ATGCTGCCAGAAAAAGACAGCTGGACTGTCAATGACATACAGAAGTTAGTGGGAAAATTA
AATTGGGCAAGTCAGATTTATGCAGGGATTAAAGTAAAGAACTTATGTAAACTCCTTAGG
GGAACCAAAGCACTAACAGAAGTAATACCACTAACAGAAGAAGCAGAGCTAGAACTGGCA
GAAAACAGGGAGATTCTAAAAGAACCAGTACATGGAGYGTATTATGACCCATCAAAAGAC
TTAGTAGCAGAATTACAGAAACAGGGACAAGGCCAATGGACATATCAAATTTATCAAGAG
CCATTTAAAAATCTGAAAACAGGAAAGTATGCAAGAATGAGGGGTGCCCACACTAATGAT
GTAAAACAGTTAACAGAGGCAGTGCAAAAAATAACCCAAGACAGGATAGTAATATGGGGA
AAGACTCCTAAATTTAAACTACCCATACAAAAAGAAACATGGGAAGCATGGTGGACGGAG
TATTGGCAAGCCACCTGGATTCCTGAATGGGAGTTTGTCAATACCCCTCCCTTAGTAAAA
TTATGGTACCAGTTAGAGAAAGACCCCATAGTAGGAGCAGAAACTTTCTATGTAGATGGG
GCAGCTAATAGGGAGACTAAATTAGGAAAAGCAGGATATGTTACTGACAGAGGAAGACAG
AAAGTTGTCTCCCTAACTGACACAACAAATCAGAAGACTGAATTACAAGCAATTCATCTA
GCTCTGCAGGATTCGGGATTAGAAGTAAACATAGTAACAGACTCACAATATGCATTAGGA
ATCATTCAAGCACAACCAGATAAAAGTGAATCAGAGTTAGTCAGTCAAATAATAGAGCAG
TTAATAAAAAAGGAAAAGGTCTACCTGGCATGGGTACCAGCACACAAAGGAATTGGAGGA
AATGAACAAGTAGATAAATTAGTCAGTGCTGGAATCAGGAAAGTACTATTTTTGGATGGA
```

FIG. 9-1

```
ATAGATAAGGCCCAAGAGGAACATGAGAAATATCACAGTAACTGGAGAGCAATGGCTAGT
GATTTTAACCTGCCACCTGTAGTAGCAAAAGAAATAGTAGCCAGCTGTGATAAATGCCAG
CTAAAAGGAGAAGCCATGCATGGACAAGTAGACTGTAGTCCAGGAATATGGCAACTAGAT
TGTACACATTTAGAAGGAAAAATTATCCTGGTAGCAGTTCATGTAGCCAGTGGATATATA
GAAGCAGAAGTTATTCCAGCAGAGACAGGGCAGGAAACAGCATACTTTATCTTAAAATTA
GCAGGAAGATGGCCAGTAAAAACAATACATACAGACAATGGCAGCAATTTCACCAGTACT
ACGGTTAAGGCCGCCTGTTGGTGGGCAGGGATCAAGCAGGAATTTGGCATTCCCTACAAT
CCCCAAAGTCAAGGAGTAGTAGAATCTATGAATAATGAATTAAAGAAAATTATAGGACAT
GTAAGAGATCAGGCTGAACATCTTAAGACAGCAGTACAAATGGCAGTATTTATCCACAAT
TTTAAAAGAAAAGGGGGGATTGGGGGGTACAGTGCAGGGGAAAGAATAGTAGATATAATA
GCTACAGACATACAAACTAAAGAACTACAAAAACAAATTACAAAAATTCAAAATTTTCGG
GTTTATTACAGGGACAGCAGAGAACCACTTTGGAAAGGACCAGCAAAGCTTCTTTGGAAA
GGTGAAGGGGCAGTAGTAATACAAGATAATAGTGACATAAAAGTAGTGCCAAGAAGGAAA
GCAAAGATCATTAGGGATTATGGAAAACAGATGGCAGGTGATGATTGTGTGGCAAGTAGA
CAGGATGAGGATTAGAACATGGAAAAGTTTAGTAAAACACCATATGTATGTTTCAAAGAA
AGCTAAGGGATGGTTTTATAGACATCACTATGAAAGCACTCATCCAAGAATAAGTTCAGA
AGTACACATCCCACTAGGGGATGCTACCTTGGTAGTAACAACATATTGGGGTCTGCATAC
AGGAGAAAGAGAATGGCATTTGGGCCAGGGAGCCTCTATAGAATGGAGGAAAAAGAGATA
TAGCACACAAGTAGACCCTGGCCTAGCAGACCAACTAATTCATACATATTATTTTGATTG
TTTTTCAGAATCTGCTATAAGAAATGCCATACTAGGAAATATAGTTAGTCCTAGGTGTGA
ATATCCAGCAGGACATAACAAGCTAGGATCTCTACAATACTTGGCACTAGCAGCATTGAT
AAAACCAAAAAAGATAAAGCCACCTTTGCCTAGTGTTACGAAACTAACAGAGGATAGATG
GAACAAGCCCCAGAAGACCAAGGGCCACAGAGGGAGCCATACAATGAATGGACACTAGAG
CTTTTAGAGGAGCTTAAGAGTGAAGCTATTAGACATTTTCCTAGGATATGGCTCCATAGC
TTAGAACAATACATCTATGAAACTTATGGGGATACTTGGGAAGGAGTGGAAGCCATAATA
AGAATGCTGCAACAACTGCTGTTTATTCATTTCAGAATTGGGTGTCAACATAGCAGAATA
GGCATTACTCGACAGAGAAGAGCAAGAAATGGAGCCAGTAGATCCTAGACTAGAGCCCTG
GAAGCATCCAGGAAGTCAGCCTAAGACTGCTAGTAACAATTGCTATTGTAAAAGGTGTTG
CCTTCACTGTCAAGTTTGTTTCACAAAAAAGGCTTAGGCATTTCCTATGGCAGGAAGAA
GCGGAGACAGCGACGAAGAGCTCCTCAAGACAGTAAGACTCATCAAGTTTCTCTATCAAA
GCAGTAAGTAATACATGTAATATACTCTTTACAAATATTAGCAATAGTAGCATTAGTAGT
AGTAACAATAATAGCAATAGTTGTGTGGACCATAGTACTCTTAGAATATAGGAAAATATT
AAGACAAAGAAAAATAGACAGGTTAATTGATAGAATAAGAGAAAGAGCAGAAGACAGTGG
CAATGACAGCGAGGGGGACCAGGAAGAATTATCAGCGCTTGTGGAGATGGGGCACCATGC
TCCTTGGGATGTTGATGATATGTAGTGCTGCAGAAAATTTGTGGGTCACAGTCTATTATG
GGGTCCCTGTGTGGAAAGAAGCAACCACCACTCTATTCTGTGCATCAGATGCTAGAGCAT
ATGCTACAGAGGTACATAATGTTTGGGCCACACATGCCTGTGTACCCACAGACCCCAACC
CACAAGAAGTAGTATTGGGAAATGTGACAGAAAATTTTGACATGTGGAAAAATAATATGG
TAGAACAAATGCAAGAAGATATAATCAGTTTATGGGATCAAAGCCTAAAGCCATGTGTAA
AATTAACCCCACTCTGTGTTACTTTAGATTGCACTGATGTTAATACCACTAGTAGTAGTT
TGAGGAATGCTACTAATACCACAAGTAGTAGTTGGGAAACGATGGAGAAAGGAGAATTAA
AAAACTGCTCTTTCAATACCACCACAAGCATAAGAGATAAGATGCAGGAACAATATGCAC
TTTTTTATAAACTTGATGTATTACCAATAGATAAGAATGATACTAAATTTAGGTTAATAC
ATTGTAACACCTCAACCATTACACAGGCCTGTCCAAAGATATCCTTTGAGCCAATTCCCA
TGCTTTATTATTGTACTCCGGCTGGTTTTGCGATTCTAAAGTGTAATGATAAGAAGTTCA
ATGGAACAGGACCATGTACAAATGTCAGCACAGTACAATGTACACATGGAATTAAGCCAG
TAGTGTCAACTCAACTGCTGTTAAATGGCAGCCTAGCAGAAGAAGAGGTAATAATTAGAT
CTAGCAATTTCACAAACAATGCTAAAATCATAATAGTACAGCTGAATAAATCTGTAGAAA
TTAATTGTACAAGACCCAACAACAATACAAGAAACAGGATATCAATAGGACCAGGGAGAG
CATTTCATACAACAAAACAAATAATAGGAGATATAAGACAAGCACATTGTAACCTTAGTA
GAGCAACATGGGAGAAAACTTTAGAACAGATAGCTACAAAATTAAGAAAACAATTTAGGA
ATAAAACAATAGCCTTTGATCGATCCTCAGGAGGGGATCCAGAAATTGTAATGCACAGTT
TTAATTGTGGAGGGGAATTTTTCTACTGTAATACATCACAACTGTTTAATAGTACTTGGA
ATGATACTACAAGGGCAAATAGCACTGAAGTAACTATCACACTCCCATGTAGAATAAAAC
AAATTGTAAACATGTGCCAGGAAGTAGGAAAAGCAATGTATGCCCCTCCCATCAGTGGAC
AAATTAGATGTTCATCAAAGATTACAGGGCTGCTATTAACAAGAGATGGTGGTAAGAACA
CCACGAACGGGATCGAAATCTTCAGACCTGCAGGAGGAGACATGAGGGACAATTGGAGAA
GTGAATTATATAAATATAAAGTAGTAAAAATTGAACCATTAGGAGTAGCACCCACCAAGG
CAAGGAGAAGAGTGGTGCAGAGAGAAAAAAGAGCAGTGGGAATGCTAGGAGCTATGTTCC
TTGGGTTCTTGGGAGCAGCAGGAAGCACTATGGGCGCACGGTCGATGACCGTGACGGTAC
AGGCCAGACAATTATTGTCTGGTATAGTGCAGCAGCAGAACAATCTGCTGAGGGCTATTG
AGGCGCAACAGCACCTGTTGCAACTCACAGTCTGGGGCATCAAGCAGCTCCAGGCAAGAG
TCCTGGCTGTGGAAAGATACCTAAAGGATCAACAGCTCCTAGGGATTTGGGGTTGCTCTG
```

FIG. 9-2

```
GAAAGCTCATTTGCACCACTACTGTGCCTTGGAATGCTAGTTGGAGTAATAAATCTCTGA
ATGAGATTTGGGATAACATGACCTGGATGCAGTGGGAAAGAGAAATTGACAATTACACAC
ACTTAATATACACCTTAATTGAAGAATCGCAGAACCAACAGGAAAAGAATGAACAAGAAT
TATTGGAATTGGATAAGTGGGCAGGTTTGTGGAGTTGGTTTAGCATAACAAACTGGCTGT
GGTATATAGGAATATTCATAATAATAATAGTAGGAGGCTTGGTAGGTTTAAGAATAGTTT
TTGCTGTACTTTCTATAGTGAATAGAGTTAGGCAGGGATACTCACCATTATCGTTTCAGA
CCCGCCTCCCAACCCAGAGGGGACCCGACAGGCCCGAAGGAATCGAAGAAGAAGGTGGAG
AGAGAGACAGAGACAGATCCGGAAGATTAGTGGATGGATTCTTAGCACTTATCTGGGACG
ATCTGCGGAGCCTGTGCCTCTTCAGCTACCACCGCTTGAGAGACTTAATCTTGATTGTAG
CGAGGATTGTGGAACTTCTGGGACGCAGGGGGTGGGAAGTCCTGAAATATTGGTGGAATC
TCCTGCAGTATTGGAGCCAGGAACTAAAGAATAGTGTCATTAGCTTGCTCAACGCCACAG
CTATAGCAGTAGCTGAGGGGACAGATAGGGTTATAGAAATAGTACAAAGAGCTTATAGAG
CTTTTCTCAATATACCTAGAAGAATAAGACAGGGCTTGGAAAGGGCTTTGCTATAAGATG
GGTGGCAAGTGGTCAAAATGTAGTATGAAGGGATGGCCTACTATAAGGGAAAGAATGAAG
CGAGCTGAGCTACAGCCACCTGAGCCAGCAGCAGAAGGGGTGGGAGCAGCATCTCGAGAC
CTGGAAAAACATGGAGCAATCACTAGTAGCAATACAGCAGCTACTAATGCTGATTGTGCC
TGGCTAGAAGCACAAGAGGATGAAGAGGTGGGTTTTCCAGTCAGACCTCAGGTACCTTTA
AGACCAATGACTTACAAGGGAGCTTTAGATCTTAGCCACTTTTTAAAAGAAAAGGGGGGA
CTGGAAGGGCTAATTTACTCCCAGAAAAGACAAGATATTCTTGATCTGTGGGTCTATCAC
ACACAAGGCTATTTCCCTGATTGGCAGAACTACACACCAGGGCCAGGGATCAGATATCCA
CTGTGCTTTGGATGGTGCTTCAAGTTAGTACCAATGGATCCAGACCAGGTAGAAGAGGCC
AACGAAGGAGAGAACAACAGCTTGTTACATCCTATAAGCCTGCATGGGATGGATGACCCA
GAGAAAGAAGTGTTAGTGTGGAAGTTTGACAGCCGCCTAGCATTTCGTCACATGGCCCGA
GAGGTGCATCCGGAGTACTACAAAGACTGCTGACATCGAGCTTTCTACAGGGGACTTTCC
GCTGGGGACTTTCCAGGGAGGCGTGGCCTGGGCGCGGGACCGGGGAGTGGCGAGCCCTCA
GATGCTGCATATAAGCAGCTGCTTTTTGCCTGTACTGGGTCTCTCTAGCTAGACCAGATC
TGAGCCCGGGAGCTCTCTGGCTAACTAGGGAACCCACTGCTTAAGCCTCAATAAAGCTTG
CCTTGAGTGCTTCA
```

FIG. 9-3

```
                                    Signal
                                    Peptide            gp120
          10          20          30          40          50
MTARGTRKNYQRLWRWG----TMLLGMLMICSAAENLWVTVYYGVPVWKEATTTLFCASD←HIV_OYI
 ::  :: :::::::: :    ::::::::::: :::::::::::::::::::::::::
MRVKEKYQHLWRWGWKWGTMLLGILMICSATEKLWVTVYYGVPVWKEATTTLFCASD←HIV_BRU
          10          20          30          40          50

60          70          80          90         100         110
ARAYATEVHNVWATHACVPTDPNPQEVVLGNVTENFDMWKNNMVEQMQEDIISLWDQSLK
 :: ::::::::::::::::::::::::::: :::::: :::::: ::::::::::::
AKAYDTEVHNVWATHACVPTDPNPQEVVLVNVTENFNMWKNDMVEQMHEDIISLWDQSLK
          60          70          80          90         100         110

120         130         140         150         160
PCVKLTPLCVTLDCTDVNTTSSSLRNATNTTSSSWET------MEKGELKNCSFNTTSI
::::::::::  : :::      :::::: :::: :       ::::: ::::: : ::
PCVKLTPLCVSLKCTD-------LGNATNTNSSSNTNSSSGEMMMEKGEIKNCSFNISTSI
          120         130         140         150         160

180         190         200         210         220
RDKMQEQYALFYKLDVLPIDKNDTKFRLIHCNTSTITQACPKISFEPIPMLYYCTPAGFA
: : ::::: ::::: :::: ::: : :::::: ::::::::: ::::::: : ::::
RGKVQKEYAFFYKLDIIPIDNDTTSYTLTSCNTSVITQACPKVSFEPIPIHY-CAPAGFA
          180         190         200         210         220

240         250         260         270         280
ILKCNDKKFNGTGPCTNVSTVQCTHGIKPVVSTQLLLNGSLAEEEVIIRSSNFTNNAKII
::::: :::::::::::::::::::: ::::::::::::::::::::: :: ::::::
ILKCNNKTFNGTGPCTNVSTVQCTHGIRPVVSTQLLLNGSLAEEEVVIRSANFTDNAKTI
          230         240         250         260         270         280

300         310         320         330         340
IVQLNKSVEINCTRPNNNTRNRISI--GPGRAFHTTKQIIGDIRQAHCNLSRATWEKTLE
::::: :::::::::::::: : ::   ::::: : ::  : ::::::: :: :: ::
IVQLNQSVEINCTRPNNNTRKSIRIQRGPGRAFVTIGKI-GNMRQAHCNISRAKWNATLK
          290         300         310         320         330         340

350         360         370         380         390         400
QIATKLRKQFRN-KTIAFDRSSGGDPEIVMHSFNCGGEFFYCNTSQLFNSTWNDTTRA--
:::: ::: :   ::: : ::::::::::: ::::::::::: ::::::::: :::
QIASKLREQFGNNKTIIFKQSSGGDPEIVTHSFNCGGEFFYCNSTQLFNSTWFNSTWSTE
          350         360         370         380         390         400

410         420         430         440         450
--NSTEV--TITLPCRIKQIVNMWQEVGKAMYAPPISGQIRCSSKITGLLLTRDGGKNTT
    :    :::::::::: ::::::::::::::::::::::: :::::::::::
GSNNTEGSDTITLPCRIKQFINMWQEVGKAMYAPPISGQIRCSSNITGLLLTRDGGNNN-
          410         420         430         440         450         460
```

FIG. 10-1

```
                                              gp120 ←   → gp41
        470         480        490        500        510
NGIEIFRPAGGDMRDNWRSELYKYKVVKIEPLGVAPTKARRRVVQREKRAVGMLGAMFLG
::: ::::: :::::::::::::::::::::::::::::: ::::::::::: : ::::
NGSEIFRPGGGDMRDNWRSELYKYKVVKIEPLGVAPTKAKRRVVQREKRAVGI-GALFLG
        470         480        490        500        510        520

530        540        550        560        570
FLGAAGSTMGARSMTVTVQARQLLSGIVQQQNNLLRAIEAQQHLLQLTVWGIKQLQARVL
::::::::::::::: ::::::::::::::::::::::::::::::::::::::::: :
FLGAAGSTMGARSMTLTVQARQLLSGIVQQQNNLLRAIEAQQHLLQLTVWGIKQLQARIL
    530        540        550        560        570        580

590        600        610        620        630
AVERYLKDQQLLGIWGCSGKLICTTTVPWNASWSNKSLNEIWDNMTWMQWEREIDNYTHL
::::::::::::::::::::::::::::  :::::::::: :: ::::: :::: :: :
AVERYLKDQQLLGIWGCSGKLICTTAVPWNASWSNKSLEQIWNNMTWMEWDREINNYTSL
        590        600        610        620        630        640

650        660        670        680        690
IYTLIEESQNQQEKNEQELLELDKWAGLWSWFSITNWLWYIGIFIIIIVGGLVGLRIVFA
:  ::::::::::::::::::::::::: :: ::::::::::::::: : :::::::::
IHSLIEESQNQQEKNEQELLELDKWASLWNWFNITNWLWYIKIFIMI-VGGLVGLRIVFA
    650        660        670        680        690        700

710        720        730        740        750
VLSIVNRVRQGYSPLSFQTRLPTQRGPDRPEGIEEEGGERDRDRSGRLVDGFLALINDDL
::::::::::::::::::: ::::::::::::::::::::::::: ::::: ::::::::
VLSIVNRVRQGYSPLSFQTHLPTPRGPDRPEGIEEEGGERDRDRSSRLVNGSLALINDDL
    710        720        730        740        750        760

770        780        790        800        810
RSLCLFSYHRLRDLILIVARIVELLGRRGWEVLKYWWNLLQYWSQELKNSVISLLNATAI
:::::::::::::: ::::: ::::::::::: :::::::::::::::: :::::::::
RSLCLFSYHRLRDLLLIVTRIVELLGRRGWEALKYWWNLLQYWSQELKNSAVSLLNATAI
    770        780        790        800        810        820 gp41 ←
        830        840        850
AVAEGTDRVIEIVQRAYRAFLNIPRRIRQGLERALL
::::::::::::: ::    ::::::::::::::::
AVAEGTDRVIEVVQGACRAIRHIPRRIRQGLERILL
        830        840        850        860
```

FIG. 10-2

ISOLATION, MOLECULAR CLONING AND SEQUENCING OF AN HIV-1 ISOLATE FROM A GABONESE DONOR

BACKGROUND OF THE INVENTION

This invention relates to a new strain of Human Immunodeficiency Virus (HIV), which is the major etiological agent of Acquired Immune Deficiency Syndrome (AIDS). More particularly, this invention relates to the new strain, products derived from the new strain, a diagnostic method for detecting antibodies to the strain in biological fluids, and to a diagnostic kit for carrying out the method.

An important genetic polymorphism has been recognized for the human retrovirus at the origin of Acquired Immune Deficiency Syndrome (AIDS) and other diseases, such an Lymphadenopathy Syndrome (LAS), AIDS-related complex (ARC), and possibly some encephalopathies (for review see Weiss, 1984). Indeed many of the isolates analyzed have a distinct restriction map, even if recovered from the same place and time (Benn et al., 1985). Identical restriction maps have been observed for the first two isolates designated Lymphadenopathy-Associated Virus, LAV (Alizon et al., 1984) and Human T Cell Lymphotropic Virus Type 3, HTLV-3 (Hahn et al., 1984), and thus appear as an exception.

The genetic polymorphism of the AIDS virus was better assessed after the determination of the complete nucleotide sequence of LAV (Wain-Hobson et al., 1985), HTLV-3 (Ratner et al., 1985; Muesing et al., 1985), and of a third isolate designated AIDS-associated retrovirus, ARV 2 (Sanches Pescador et al., 1985). In particular it appeared that, besides the nucleic acid variations responsible for restriction map polymorphism, isolates could differ significantly at the protein level, especially in the envelope (up to 13% difference between ARV and LAV), by both amino acid substitutions and reciprocal insertion-deletion (Rabson and Martin, 1985).

Clinical and epidemiological studies have highlighted the presence and recent spread of AIDS and associated diseases in Central Africa (Piot et al., 1984; Van de Perre et al., 1984; Clumeck et al., 1984; Montaqnier, 1985). They have also revealed that transmission principally occurs through heterosexual contacts, unlike in the developed countries, and from mother to child. In fact, a much larger fraction of the population is exposed to AIDS than in the USA or Europe, hence the notion that AIDS is endemic to Central Africa. In spite of these epidemiological peculiarities, a retrovirus that is structurally and biologically indistinguishable from the European or American isolates and whose proteins are antigenically indistinguishable was found in patients and in healthy carriers originating from central Africa (Elrodt et al., 1984; Brun-Vezinet et al., 1984; Bailey et al., 1985).

Given the distant geographical origins of the retrovirus from African and U.S. patients, the significant differences in their respective isolates, and differences in modes of transmission, there exists a need in the art for information on genetic polymorphism of the virus. More particularly, there exists a need in the art to investigate the genetic variability of the AIDS virus, in particular its range, the underlying mechanisms, and the apparent existence of hypervariable or well conserved domains in the viral proteins Indeed, such conserved domains are likely to be associated with important biological functions, and their delineation would be a step towards understanding the molecular mechanisms of viral pathogenicity. Furthermore, identification of the retroviruses must be considered for the development of genetically engineered proteins for therapeutic purposes.

SUMMARY OF THE INVENTION

This invention aids in fulfilling these needs in the art. More particular, this invention provides a human retrovirus, wherein the retrovirus is a retroviral variant of Human Immunodeficiency Virus (HIV), and wherein (a) the retroviral variant is capable of being immunologically recognized by antibodies to gag and pol gene products of HIV-1 and HIV-2 when assayed by Western Blot technique;

(b) the retroviral variant is not immunologically recognized by antibodies to envelope glycoproteins gp 160, gp 120 and gp 41 of HIV-1 or HIV-2 when assayed by Western Blot technique; and (c) the retroviral variant exhibits weaker immunologic reaction to the gene products of HIV-2 than to the gene products of HIV-1.

The retroviral variant is in biologically pure form.

This invention also provides a human retrovirus, wherein the retrovirus is a variant of Human Immunodeficiency Virus (HIV), and the variant is retrovirus HIV-1 OYI, and mutants and variants thereof, in a purified form. Isolates and suspensions of the retrovirus in a buffer are provided.

In addition, this invention provides antigen of the human retrovirus of the invention wherein the antigen is in a purified form and is capable of being immunologically recognized by human body fluid containing antibodies to the retrovirus. The antigen can be a protein of the retrovirus, such as a core protein or an envelope protein of the retrovirus.

An immunological complex between antigen of the invention and an antibody recognizing said antigen is also provided. The immunological complex can be labeled with an immunoassay label selected from the group consisting of radioactive, enzymatic, flourescent, chemiluminescent labels and chromophores.

This invention further provides a polypeptide of the human retrovirus of the invention, wherein the polypeptide is in a purified form.

This invention also provides a structural protein of the human retrovirus of the invention, wherein the protein is gp41 in a purified form or gp110 in a purified form.

Genomic DNA of the human retrovirus of the invention is also provided. The DNA is in a purified form and has a nucleotide sequence substantially corresponding to the nucleotide sequence for HIV OYI. The DNA can have a nucleotide sequence encoding for all or part of a protein selected from the group consisting of GAG, POL, ORF Q, ORF R, TAT, ART, ENV and ORF F proteins of the retrovirus.

Plasmid pOYI10 having the characteristics of the plasmid deposited under culture collection accession number CNCM I-694 is provided.

Plasmid pOYI12 having the characteristics of the plasmid deposited under culture collection accession number CNCM I-695 is also provided.

This invention also encompasses a labeled antigen of the human retrovirus of the invention wherein the antigen is capable of being immunologically recognized by human body fluid containing antibodies to the retrovirus. The antigen can be labeled with an immunoassay label selected from the group consisting of radioactive, enzymatic, fluorescent, chemiluminescent labels and chromophores.

An extract of the human retrovirus is provided, wherein the extract comprises antigen of the retrovirus and the antigen is in purified form and is capable of being immunologically recognized by human body fluid containing antibodies to the retrovirus.

A lysate of the retrovirus is also provided, wherein the lysate comprises antigen of the retrovirus and the antigen is in purified form and is capable of being immunologically recognized by human body fluid containing antibodies to the retrovirus. The lysate can comprise crude lysate of the retrovirus, or it can consist essentially of a lysate of a biologically pure culture of the retrovirus.

A supernatant of a cell culture infected with the retrovirus is provided, wherein the supernatant comprises antigen of the retrovirus and the antigen is capable of being immunologically recognized by human body fluid containing antibodies to the retrovirus. The supernatant can comprise the retrovirus in suspension therein, or the supernatant can be substantially cell-free.

An in vitro diagnostic method for the detection of the presence or absence of antibodies which bind to an antigen of the invention is provided. The method comprises contacting the antigen of the retrovirus with a biological fluid for a time and under conditions sufficient for the retroviral antigen and antibodies in the biological fluid to form an antigen-antibody complex; and detecting the formation of the complex. The detecting step can further comprise measuring the formation of the antigen-antibody complex. The formation of the antigen-antibody complex is preferably measured by immunoassay based on Western Blot technique or ELISA (enzyme linked immunosorbent assay) or indirect immunofluorescent assay.

A diagnostic kit for the detection of the presence or absence of antibodies which bind to antigen of the human retrovirus of the invention is also provided. The kit comprises antigens of the retrovirus; and means for detecting the formation of immune complex between the antigens and the antibodies. The antigens and the means are present in an amount sufficient to perform the detection.

BRIEF DESCRIPTION OF THE DRAWINGS

This invention will be more fully understood by reference to the drawings in which:

FIG. 1 depicts the protein sequence of the GAG protein of HIV-1 OYI of the invention in comparison with AIDS retroviral isolate LAV$_{BRU}$;

FIG. 2 depicts the protein sequence of the POL protein of HIV-1 OYI of the invention in comparison with AIDS retroviral isolate LAV$_{BRU}$;

FIG. 3 depicts the protein sequence of the open reading frame (ORF) Q protein of HIV-1 OYI of the invention in comparison with AIDS retroviral isolate LAV$_{BRU}$;

FIG. 4 depicts the protein sequence of the ORF R protein of HIV-1 OYI of the invention in comparison with AIDS retroviral isolate LAV$_{BRU}$;

FIG. 5 depicts the protein sequence of the TAT protein of HIV-1 OYI of the invention in comparison with AIDS retroviral isolate LAV$_{BRU}$;

FIG. 6 depicts the protein sequence of the ART protein of HIV-1 OYI of the invention in comparison with AIDS retroviral isolate LAV$_{BRU}$;

FIG. 7 depicts the protein sequence of the ENV protein of HIV-1 OYI of the invention in comparison with AIDS retroviral isolate LAV$_{BRU}$;

FIG. 8 depicts the protein sequence of the ORF F protein of HIV-1 OYI of the invention in comparison with AIDS retroviral isolate LAV$_{BRU}$;

FIG. 9 depicts the nucleotide sequence of HIV-1 OYI of the invention;

FIG. 10 depicts a more detailed comparison of the protein sequence of the ENV protein of HIV-1 OYI of the invention with AIDS retroviral isolate LAV$_{BRU}$;

DETAILED DESCRIPTION OF PREFERRED EMBODIMENTS

Figure 11:
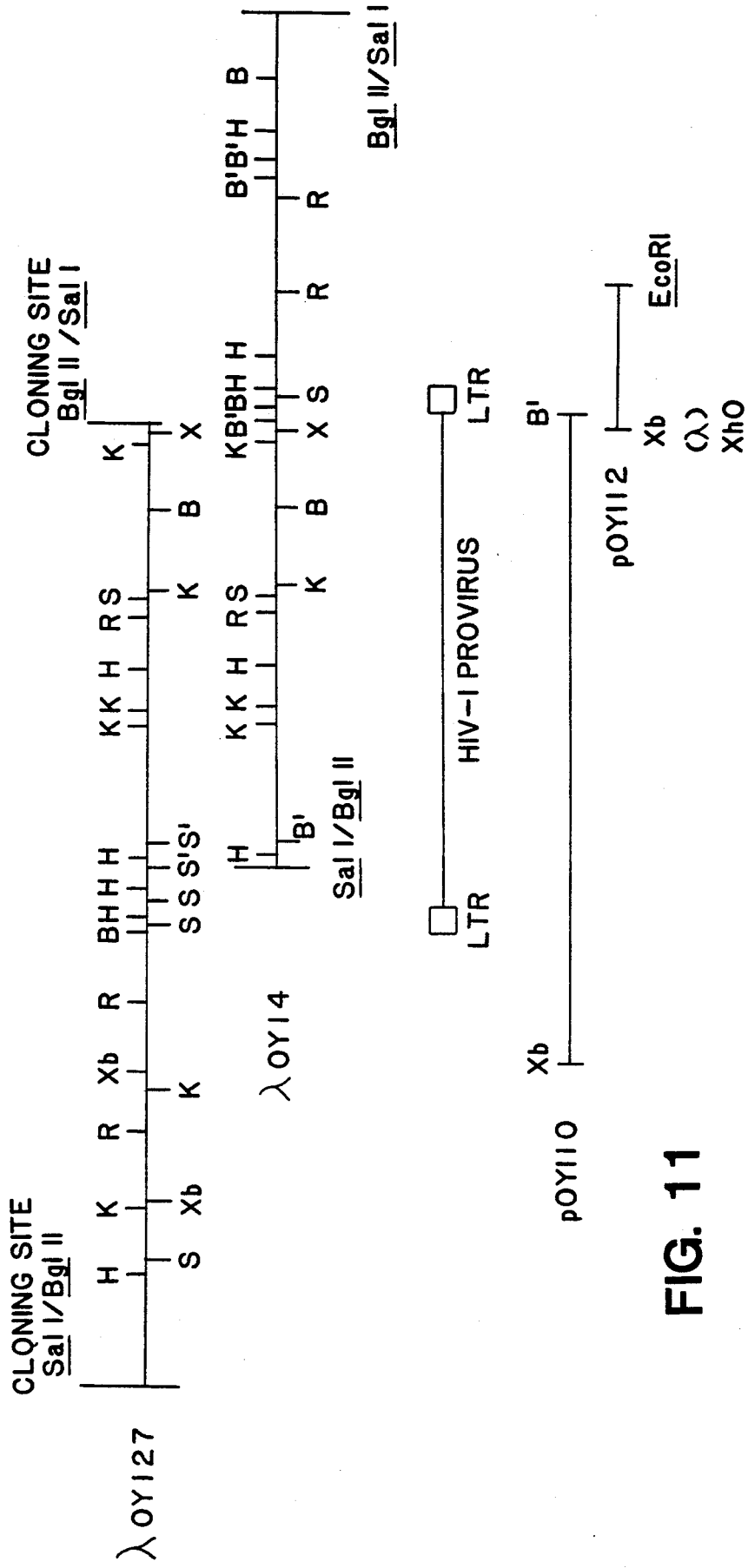
FIG. 11 is a restriction map of overlapping phage lambda clones.

During a serological survey for human AIDS viruses in the Gabon, an unusual Western Blot (WB) profile was observed amongst a group of 24 pregnant women who were without any sexually transmitted diseases. Sera from all 24 women detected readily the HIV-1 gag and pol gene products on an HIV-1 WB, but failed to detect the envelope glycoproteins gp160, gp120 and gp41. The sera showed strong recognition of p25 protein of HIV-1 viral gag and pol gene products, yet the reaction was systematically weaker suggesting that the virus is an HIV-1 variant, and not an HIV-2 variant. No envelope reactivity to HIV-2 envelope antigens was detected.

It must be emphasized that to date none of these women has any clinical signs of AIDS or AIDS prodromes whatsoever. AIDS is recognized in Gabon, but in all cases examined so far, these patients have been infected by a typical HIV-1, i.e., sera from these patients detects all the HIV-1 proteins on a Western Blot.

Intriguingly, the children born to the 24 mothers carried only maternal antibody as evidenced by the fiact that after 12 months of follow-up none of the 24 children carried any antibodies to HIV-1. All children were well.

Given this unusual serology and accompanying absence of apparent disease, three isolates (No. 396, No. 397 and No. 398) were derived from frozen lymphocyte suspensions. Virus was first identified as to reverse transcriptase activity in the culture supernatant from day 20 onwards. The titres were low (between 50–100K cpm/ml), yet stable thereafter to 8 weeks. No cytopathic effect or giant-cell formation was observed throughout the culture. The absence of these two phenomena are characteristic of this particular virus.

In agreement with the recommendations of the WHO Working Group on the characterization of HIV-related retroviruses, the virus (N° 396) has been identified HIV-1-OYI/Gabon/86:

OYI — refers to the patient;

Gabon — country of origin of isolate; and

86 — year of isolation.

High molecular weight DNA from HIV1-OYI/Gabon/86 infected cells was extracted (Wain-Hobson, Bishop and Dejean, 1984, Editions INSERM, constitution de banques d'AND génomiques á l'aide de phage ou de cosmides) and subjected to restriction endonuclease, Southern blotting and molecular hybridization using an HIV-1 probe under stringent conditions.

| Uncut:   | 10 kb                            |
|----------|----------------------------------|
| BamHI:   | 7.2 kb and 2.1 kb                |
| HindIII: | 5.0 kb, 3.5 kb, 0.88 kb and 0.8 kb |
| Bgl II:  | 5.4 kb, 2.2 kb, 1.05 kb and 0.96 kb |

From this premise the provirus was cloned into the phage replacement vector EMBL3 (Frischauff et al., J. Mol. Biol., 1983, 170, 827–842). The cloning strategy is briefly described below:

1. Partial Bql II restriction of high molecular weight DNA.
2. Sucrose gradient fractionation of DNA. DNA of 15–25 kb pooled and precipitated.
3. Ligation into EMBL3 BamHI restricted arms.
4. In vitro packaging of ligated DNA.
5. Plating out and screening in situ using an HIV-1 probe under stringent conditions.
6. Plaque purification of positives.

Nine positive phage λ clones were isolated. However, clones λ OYI27 and λ OYI4 cover the whole provirus. A restriction map of both clones and their relationship to the integrated provirus is shown in FIG. 11. The following abbreviations are used in FIG. 11 to identify restriction enzyme sites:

| B  | BamH1   |
|----|---------|
| B' | BglII   |
| H  | HindIII |
| K  | KpnI    |
| R  | EcoRI   |
| S  | SaeI    |
| X  | XhaI    |
| Xb | XbaI.   |

It is evident from FIG. 11 that neither carries a whole provirus, Nevertheless, they encode between them the complete proviral genome of HIV-1 OYI.

The isolate OYI127 carries 5' cellular flanking sequences:
5' LTR; and
gag, pol, Q, R, tat, T, art, env gene sequences.

The isolate OYI carries most of gag;
All of pol, Q, R, tat, art, env and F gene sequences;
a 3' LTR; and
3' cellular flanking sequences.

Two plasmid subclones have been derived which together contain the whole provirus. These are plasmids pOYI10 and pOYI12 (FIG. 11). These two plasmids encompass between them the complete viral genome of HIV OYI.

Plasmid pOYI10 was derived from phage λ OYI27 and carries the XbaI-BqlII sites. The insert is 11kb and carries all the HIV-1 sequences present in λ OY127. It differs in that it carries less 5' cellular flanking DNA.

Plasmid pOYI12 was derived from phage λ OY14 and carries an XbaI-EcoRI fragment of 1.8kb. It carries all the HIV proviral sequences lacking in clone pOYI12 and 1kb of 3' cellular flanking sequences.

The plasmids have been deposited in the Collection Nationale des Cultures de Micro-organismes (CNCM) at Institut Pasteur in Paris, France, on Oct. 7, 1987. Specifically, the plasmid pOY110 was deposited under culture collection accession No. CNCM I-694, and the plasmid pOYI12 under culture collection accession No. CNCM I-695.

The retrovirus HIV-1-OYI/Gabon/86 is also referred to herein as HIV-1 OYI or merely HIV OYI. The virus is useful because it provides a source of antigens for vaccines and for detecting antibodies to the retrovirus.

While HIV-1 OYI is specifically described herein, it will be understood that this invention includes within its scope all retroviral mutants and variants thereof. Thus, this invention includes any virus having a similar phenotype or genotype to HIV-1 OYI. This invention also includes any virus, viral protein or fragment thereof having similar patterns of immunological reaction to HIV-1 OYI. This invention further includes within its scope all extracts, isolates, lysates, cell supernatants, and cell cultures containing any of these viruses, viral proteins, or fragments of the viral proteins.

The amino acid sequences of various proteins of the retrovirus of the invention were determined. The following one letter codes are used herein to identify amino acids:

| A | Ala |
|---|-----|
| C | Cys |
| D | Asp |
| E | Glu |
| F | Phe |
| G | Gly |
| H | His |
| I | Ile |
| K | Lys |
| L | Leu |
| M | Met |
| N | Asn |
| P | Pro |
| Q | Gln |
| R | Arg |
| S | Ser |
| T | Thr |
| V | Val |
| W | Trp |
| Y | Tyr |

The amino acid sequences of the proteins are shown in FIGS. 1–8 and 10. In the Figures, the protein sequences are shown with the $NH_2$-termini in the upper left-hand corner and the COOH-termini in the lower right-hand corner.

The nucleotide sequence of the new strain of HIV-1 of the invention was derived by dideoxynucleotide sequencing and is given in FIG. 9. The base sequences of the nucleotides in FIG. 9 are written in the 5'→3' direction. Each of the letters shown in FIG. 9 is a conventional designation for the following nucleotides:

| A | Adenine  |
|---|----------|
| G | Guanine  |
| T | Thymine  |

| | |
|---|---|
| C | Cytosine. |

The protein sequences and nucleotide sequence of the retrovirus HIV-1 OYI of the present invention are aligned in the Figures with the corresponding sequences of another AIDS virus isolate, namely LAV$_{BRU}$. The isolate LAV$_{BRU}$ was the prototype AIDS virus isolated in 1983 from a French homosexual patient with LAS, thought to have been previously infected in the U.S. (*Barre-Sinnousi et al.*, 1983). A minimum number of gaps (—) were introduced in the alignments shown in the Figures. Points of identity in the sequences are indicated by a colon (:). The top line in each case is the sequence of HIV-1 OYI of the invention and the bottom line is the sequence for HIV$_{BRU}$.

FIG. 10 is a detailed comparison of the ENV protein of retrovirus rovirus HIV-1 OYI of the invention with HIV$_{BRU}$. The locations of the "signal peptide", "gp120" protein, and "gp41" protein are indicated by the arrows in the FIG. In addition, portions of the amino acid sequences are enclosed in boxes. The boxes identify regions that might account for differences in the antigenic character of the two retroviruses. Of course, the differences in antigenic character could be attributable to differences in the amino acids in each sequence.

A comparison was also made between the amino acid sequences of proteins of several HIV 1 strains, including HIV-1 OYI of the invention. The amino acid sequence of HIV$_{BRU}$, which was the first HIV variant to be sequenced, was taken as a reference. The results are shown in Table 2 in which percent differences between HIV$_{BRU}$ and the indicated HIV variants are reported.

TABLE 2

| HIV Variant | Percent Difference in Amino Acid Sequence Using BRU As The Reference | | | | | | |
|---|---|---|---|---|---|---|---|
| BRU | GAG | POL | Q (SOR) | R | TAT | ENV | F (3'orf) |
| ARV 2 | 3.4 | 3.1 | 10.0 | 9.4 | 15.0 | 13.0 | 13.5 |
| OYI | 6.8 | 4.0 | 8.4 | 11.5 | 14.1 | 15.3 | 15.0 |
| MAL | 12.0 | 7.7 | 12.6 | 10.4 | 23.8 | 21.7 | 27.0 |

Key:
BRU = HIV-1 strain isolated in Paris France from French donor.
ARV 2 = HIV-1 strain also known as SF2 from San Francisco donor. (Jay Levy et al.)
OYI = HIV-1 strain HIV-1 OIY of the invention.
MAL = HIV-1 strain isolated in France from Zairian donor.

Figure 12:
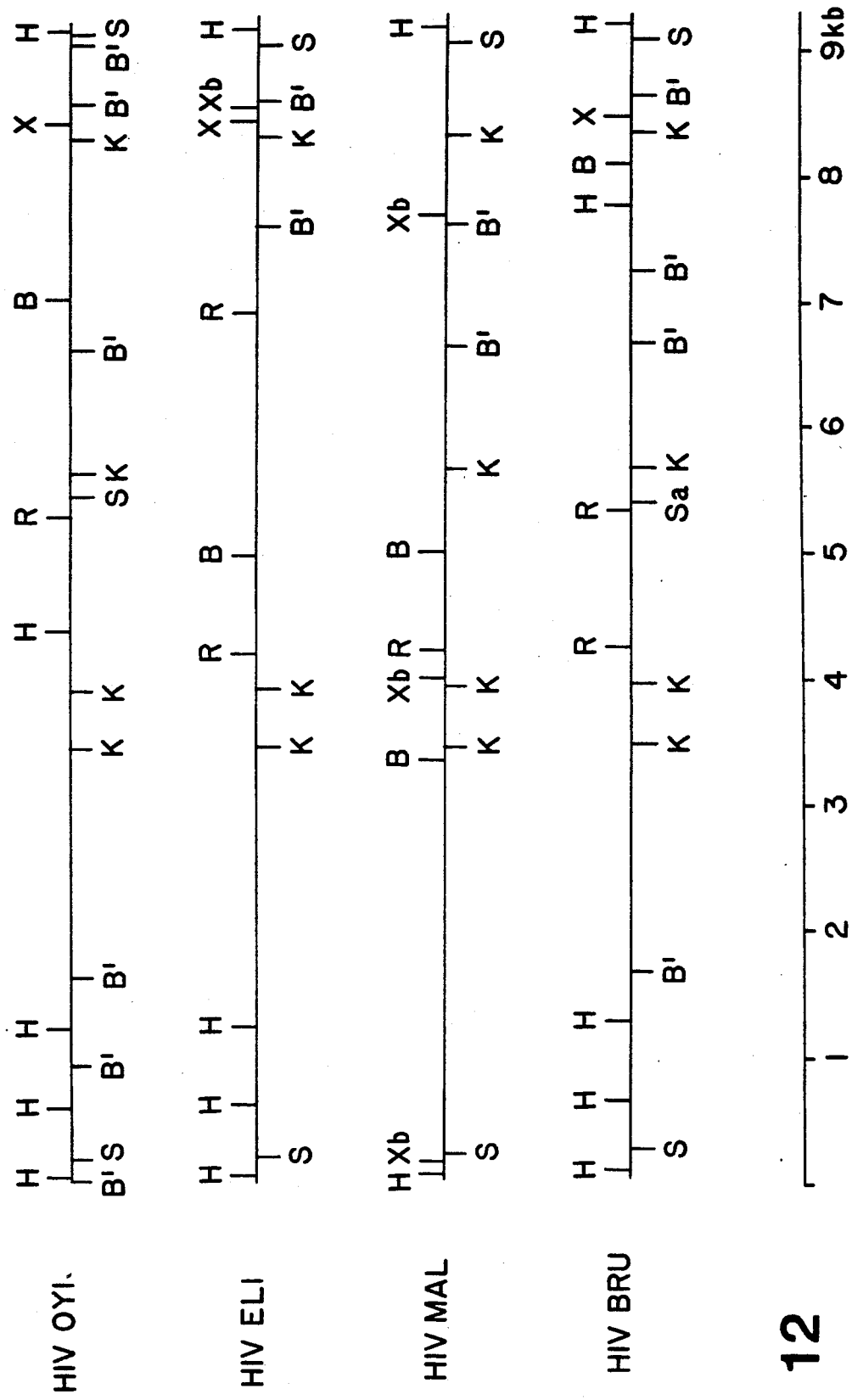
FIG. 12 is a restriction map of HIV-1 OYI RNA in comparison with other HIV-1 strains.

FIG. 12 is a restriction map of HIV OYI of the invention. The genetic structure shown in FIG. 12 is that of the RNA form of the virus, i.e. RUS gag pol Q R tat art env Fu3R. The abbreviation used to identify restriction enyzme sites are the same as in FIG. 11 with the addition of

| | |
|---|---|
| Sa | SalI. |

The restriction maps of HIV-1 strains ELI and MAL (Zairian) and BRU are included in FIG. 12 for comparison.

Figure 13:
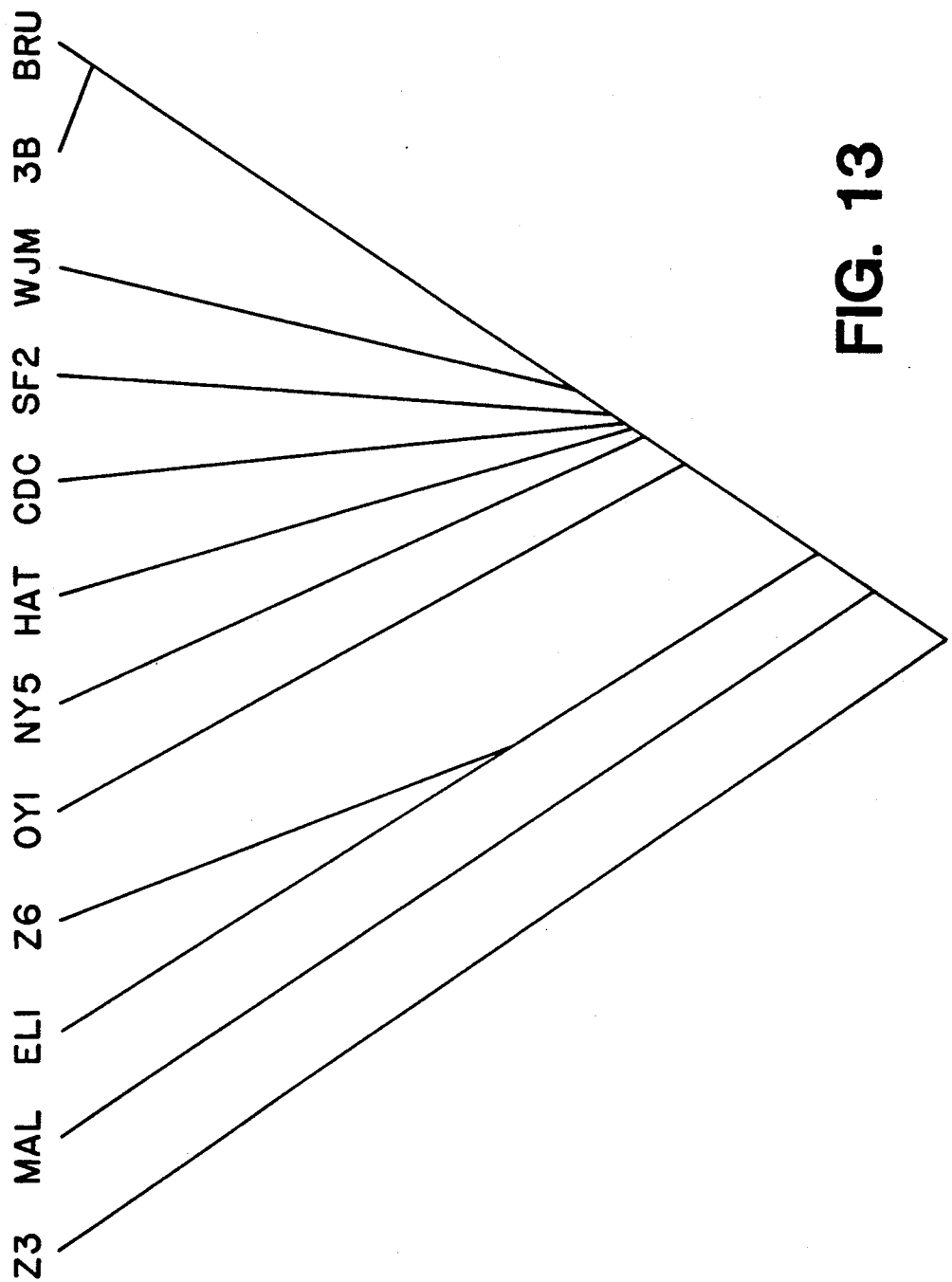
FIG. 13 is a phylogenetic tree of HIV variants based on amino acid sequence variability in glycoprotein gp120.

Finally, FIG. 13 is a phylogenetic tree of HIV-1 variants based on amino acid sequence variability of aligned protein sequences of the external glycoprotein gp120. See Sonigo et al., Cell, 42:369-382 (1985) for methodology. The following abbreviations are used in FIG. 13:

| | |
|---|---|
| Z3 | HIV of strain Z3 origin Zaire |
| MAL | HIV of strain MAL origin Zaire |
| ELI | HIV of strain ELI origin Zaire |
| Z6 | HIV of strain Z6 origin Zaire |
| OYI | HIV of strain OYI origin Gabon |
| NY5 | HIV of strain NY5 origin U.S., New York |
| HAT3 | HIV of strain HAT3 origin Haiti |
| CDC | HIV of strain CDC451 origin U.S. |
| SF2 | HIV of strain SF2/ARV2 origin U.S., San Francisco |
| WJM | HIV of strain WJM1 origin Haiti |
| 3B | HIV of strain HTLV3B origin U.S. (clone BH10) |
| BRU | HIV of strain LAV/BRU origin France. |

These strains have been described in the following references:

| | |
|---|---|
| Z3 | Willey et al. (1986), Proc. Natl. Acad. Sci. U.S.A. 83, 5038-5092 |
| MAL | Alizon et al. (1986), Cell 46, 63-74 |
| ELI | Alizon et al. (1986), Cell 46, 63-74 |
| Z6 | Srinivasan et al. (1987), Gene in press |
| OYI | This invention |
| NY5 | Willey et al. (1986), Proc. Natl. Acad. Sci. U.S.A. 83, 5038-5042 |
| HAT | Starcich et al. (1986), Cell 45, 637-648 |
| CDC | Desai et al. (1980), Proc. Natl. Acad. Sci. U.S.A. 83, 8380-8384 |
| SF2 | Sanchez-Pescador et al. (1985), Science 227, 484-492 |
| WJM | Starach et al. (1986), Cell 45, 637-698 |
| | Hahn et al. (1986), Science 232, 1548-1553 |
| 3B | Ratner et al. (1985), Nature 313, 277-284 |
| BRU | Wain-Hobson et al. (1985), Cell 40, 9-17 |

It will be understood that the present invention is intended to encompass the retroviral proteins and peptide fragments thereof whether or not glycosylated, in purified form, and whether obtained using the techniques described herein or other methods. For example, other methods include genetic engineering techniques, such as the expression in a suitable host of a DNA sequence encoding the proteins or polypeptides of the retrovirus. Other methods of course include chemical synthesis of the peptides using conventional organic chemistry techniques.

This invention also includes peptides in which a portion of the retroviral proteins containing the antigenic binding site is linked to a larger carrier molecule, such as a polypeptide or a protein, and in which the resulting product exhibits specific binding for antibodies to the retrovirus in vivo or in vitro. In this case, the polypeptide can be smaller or larger than the peptide of the invention.

It will be understood that the peptides of the invention encompass peptides having equivalent peptide sequences. By this it is meant that peptide sequences need not be identical to the sequences disclosed herein. Variations can be attributable to local mutations involving one or more amino acids not substantially affecting the antibody-binding capacity of the peptide. Variations can also be attributable to structural modifications that do not substantially affect antibody-binding capacity. Thus, for example, this invention is intended to cover serotypic variants of the proteins and peptides of the invention.

The retroviral proteins and the protein fragments of the present invention can be used to identify antibodies to the retrovirus in materials and to determine the concentration of the antibodies in those materials. Thus, the proteins and protein fragments can be used as antigens for qualitative or quantitative determination of the retrovirus in a material. Such materials of course include biological fluids, such as human body fluids, including human sera. When used as a reagent in an immunoassay for determining the presence or concentration of the antibodies to the retrovirus, the retroviral antigens of the present invention provide an assay that is convenient, rapid, sensitive, and specific.

More particularly, the antigens of the invention can be employed for the detection of the retrovirus by means of immunoassays that are well known for use in detecting or quantifying humoral components in fluids. Thus, antigen-antibody interactions can be directly observed or determined by secondary reactions, such as precipitation or agglutination. Other immunoassays in which the antigens of the present invention can be employed include, but are not limited to, radioimmunoassay, competition immunoprecipitation assay, enzyme immunosassay, and immunofluorescence assay. It will be understood that tubidimetric, colorimetric and nephelometric techniques can be employed.

Immunoassays can be carried out by immobilizing one of the immunoreagents, either the antigen of the invention or the antibodies to the retrovirus, on a carrier surface while retaining immunoreactivity of the reagent. The reciprocal immunoreagent can be unlabeled or labeled in such a manner that immunoreactivity is also retained. These techniques are especially suitable for use in enzyme immunoassays, such as enzyme linked immunosorbent assay (ELISA). An immunoassay based on Western Blot technique is particularly preferred.

Depending on the use to be made of the retroviral proteins and antigens of the invention, it may be desirable to label the proteins and antigens. Examples of suitable labels are radioactive labels, enzymatic labels, flourescent labels, chemiluminescent labels or chromophores. The methods for labeling retroviral proteins or antigens of the invention do not differ in essence from those widely used for labeling immunoglobulin. The need to label may be avoided by using labeled antibody to the retroviral antigen of the invention or anti-immunoglobulin to the antibodies to the retrovirus as an indirect marker.

According to a preferred embodiment, the invention, an antigen obtainable from a lysate of the virus is a glycoprotein having a molecular weight of the order of 110,000 dalton as determined by its migration distance in comparison with the distances of migrations, in a same migration system, of standard proteins having known molecular weights.

The viruses, proteins and antigens of the invention can be purified according to conventional techniques. For example, purification can be carried out by employing differences in molecular weights. Differential migration on a gel or gradient centrifugation can be employed. The antigens according to the invention can be separated from the lysate of the viruses by their affinity for lectins. The lectin can be immobilized on a solid support.

A more thorough purification of the antigens can be performed by immunoprecipitation with the sera of patients known to possess antibodies effective against the protein, with concentrated antibody preparations, such as polyclonal antibodies, or with monoclonal antibodies directed against the antigen of the invention.

Finally, the invention provides immunogenic polypeptides, and more particularly, protective polypeptides for use in the preparation of vaccine compositions against the retrovirus of the invention. These polypeptides could be produced by chemical synthesis or by genetic engineering techniques. They could be eventually used in combination with specific adjuvants, such as aluminium hydroxyde or equivalents, which are already accepted for human use.

More particularly, epitope-bearing polypeptides, particularly those whose N-terminal and C-terminal amino acids are free, are accessible by chemical synthesis using techniques well known in the chemistry of proteins. For example, the synthesis of peptides in homogeneous solution and in solid phase is well known.

In this respect, recourse may be had to the method of synthesis in homogeneous solution described by Houbenweyl in the work entitled "Methoden der Organischen Chemie" (Methods of Organic Chemistry), edited by E. WUNSCH, vol. 15-I and II, THIEME, Stuttgart (1974).

This method of synthesis consists of successively condensing either the successive amino acid in twos in the appropriate order, or successive peptide fragments previously available or formed and containing already several aminoacyl residues in the appropriate order, respectively. Except for the carboxyl and amino groups which will be engaged in the formation of the peptide bonds, care must be taken to protect beforehand all other reactive groups borne by these aminoacyl groups and fragments. However, prior to the formation of the peptide bonds, the carboxyl groups are advantageously activated according to methods well known in the synthesis of peptides. Alternatively, recourse may be had to coupling reactions bringing into play conventional coupling reagents for instance of the carbodiimide type such as 1-ethyl-3-(3-dimethyl-aminopropyl)-carbodiimide. When the amino acid group used carries an additional amino group (e.g. lysine) or another acid function (e.g. glutamic acid), these groups may be protected by carbobenzoxy or t-butyloxycarbonyl groups, as regards the amino groups, or by t-butylester groups, as regards the carboxylic groups. Similar procedures are available for the protection of other reactive groups. For example, SH group (e.g. in cysteine) can be protected by an acetamidomethyl or paramethoxybenzyl group.

In the case of progressive synthesis, amino acid by amino acid, the synthesis preferably starts by the condensation of the C-terminal amino acid with the amino acid which corresponds to the neighboring aminoacyl group in the desired sequence and so on, step by step, up to the N-terminal amino acid. Another preferred technique that can be relied upon is that described by R. D. Merrifield in "Solid Phase Peptide Synthesis" (J. Am. Chem. Soc., 45, 2149-2154). In accordance with the Merrifield process, the first C-terminal amino acid of the chain is fixed to a suitable porous polymeric resin by means of its carboxylic group, the amino group of said amino acid then being protected, for example, by a t-butyloxycarbonyl group.

When the first C-terminal amino acid is thus fixed to the resin, the protective group of the amino group is removed by washing the resin with an acid, i.e. trifluoroacetic acid when the protective group of the amino group is a t-butyloxycarbonyl group.

Then the carboxylic group of the second amino acid, which is to provide the second aminoacyl group of the desired peptidic sequence, is coupled to the deprotected amino group of the C-terminal amino acid fixed to the resin. Preferably, the carboxyl group of this second amino acid has been activated, for example by dicyclohexylcarbodiimide, while its amino group has been protected, for example by a t-butyloxycarbonyl group. The first part of the desired peptide chain, which comprises the first two amino acids, is thus obtained. As previously, the amino group is then deprotected, and one can further proceed with the fixing of the next aminoacyl group and so forth until the whole peptide sought is obtained.

The protective groups of the different side groups, if any, of the peptide chain so formed can then be removed. The peptide sought can then be detached from the resin, for example, by means of hydrofluoric acid, and finally recovered in pure form from the acid solution according to conventional procedures.

As regards the peptide sequences of smallest size and bearing an epitope or immunogenic determinant, and more particularly those which are readily accessible by chemical synthesis, it may be required, in order to increase their in vivo immunogenic character, to couple or "conjugate" them covalently to a physiologically acceptable and non-toxic carrier molecule.

By way of examples of carrier molecules or macromolecular supports which can be used for making the conjugates according to the invention, will be mentioned natural proteins, such as tetanic toxoid, ovalbumin, serum-albumins, hemocyanins, etc. Synthetic macromolecular carriers, for example polysines or poly(D-L-alanine)-poly(L-lysine)s, can also be used.

Other types of macromolecular carriers which can be used, which generally have molecular weights higher than 20,000, are known from the literature.

More detailed procedures for practicing this invention are available in the literature. See, e.g. PCT Published Application having International Publication No. WO86/02383 and an International Publication Date of Apr. 24, 1986.

In summary, a variant of HIV has now been identified, genomic DNA from the retrovirus has been cloned and retroviral proteins have been sequenced. In addition to providing useful tools for detection of the retrovirus in humans, this invention adds to the base of knowledge relating to genetic variability of the AIDS virus.

The following references have been referred to by author and date of publication in this specification:

Alizon, M., Sonigo, P., Barre-Sinoussi, F., Chermann, J. C., Tiollais, P., Montagnier, L., and Wain-Hobson, S. (1984). Molecular cloning of lymphadenopathy-associated virus. Nature 312, 757–760.

Bailey, A. C., Downing, R. G., Cheinsong-Popov, R., Tedder, R. C., Dalgleish, A. G., and Weiss, R. A. (1985). HTLV-III serology distinguishes atypical and endemic Kaposi's sarcoma in Africa. Lancet I, 359–361.

Benn, S., Rutledge, R., Folks, T., Gold, J., Baker, L., McCormick, J., Feorino, P., Piot, P., Quinn, T., and Martin, M. (1985). Genomic heterogeneity of AIDS retroviral isolates from North America and Zaire. Science 230, 949–951.

Brun-Vezinet, F., Rouzioux, C., Montagnier, L., Chamaret, S., Gruest, J., Barre-Sinoussi, F., Geroldi, D., Chermann, J. C., McCormick, J., Mitchell, S., Piot, P., Taelmann, H., Minlangu, K. B., Whobin, O., Mbendi, N., Mazebo, P., Kalambayi, K., Bridts, C., Desmyter, J., Feinsod, F., and Quinn, T. C. (1984). Prevalence of antibodies to lymphadenopathy-associated virus in African patients with AIDS. Science 226, 453, 456.

Clumeck, N., Sonnet, J., Taelman, M., Mascart-Lemone, F., De Bruyere, M., Van de Perre, P., Dasnoy, J., Marcelis, L., Lamy, M., Jonas, C., Eyckmans, L., Noel, H., Vanhaeverbeek, M., and Butzler, J. P. (1984). Acquired immune deficiency syndrome in African patients. N. Eng. J. Med. 310, 492–497.

Ellrodt, A., Barre-Sinoussi, F., Le Bras, P., Nugeyre, M. T., Brun-Vezinet, F., Rouzioux, C., Segond, P., Caquet, R., Montagnier, L., and Chermann, J. C. (1984). Isolation of human T-lymphotropic retrovirus (LAV) from Zairan married couple, one with AIDS, one with prodomes. Lancet I, 1383–1385.

Frischauff, A.M., Lehrach, H. et al., 1983, J. Mol. Biol., 27–842, Replacement Vectors Carrying Polylinker Sequences.

Montagnier, L. (1985). Lymphadenopathy-associated virus: from molecular biology to pathogenicity. Ann. Intern. Med. 103, 689–693.

Muesing, M. A., Smith, D. M., Cabradilla, C. D., Benton, C. V., Lasky, L. A., and Capon, D. J. (1985). Nucleic acid structure and expression of the human AIDS/lymphadenopathy retroviruses. Nature 313, 450–458.

Piot, P., Quinn, T. C., Taelmann, H., Feinsod, F. M., Minlangu, K. B., Wobin, O., Mbendi, N., Mazebo, p, Ndongi, K., Stevens, W., Kalambayi, K., Mitchell, S., Bridts, C., and McCormick, J. B. (1984). Acquired immunodeficiency syndrome in a heterosexual population in Zaire Lancet II, 65–69.

Rabson, A. B., and Martin, M. A. (1985). Molecular organization of the AIDS retrovirus. Cell 40, 477–480.

Ratner, L., Haseltine, W., Patarca, R., Livak, K. J., Starcich, B., Josephs, S. F., Doran, E. R., Rafaiski, A., Whitchorn, E. A., Baumeister, K., Ivanoff, L., Petteway, S. R. Pearson, M. L., Lautenbergen, J. A., Papas, T. S., Ghrayeb, J., Chan, N. T., Gallo, R. C., and Wong-Staal, F. (1985). Complete nucleotide sequence of the AIDS virus. HTLV-III. Nature 313, 227–284.

Sanchez-Pescador, R., Power, M. D., Barr, P. J., Steimer, K. S., Stemfeien, M. M., Brown-Shimer, S. L., Gee, W. W., Bernard, A., Randolph, A., Levy, J. A., Dina, D., and Luciw, P. A. (1985). Nucleotide sequence and expression of an AIDS-associated retrovirus (ARV-2). Science 227, 484–492.

Van de Perre, P., Rouvroy, D., Lepage, P., Bogaerts, J., Kestelyn, P., Kayihigi, J., Hekker, A. C., Butzler, J. P., and Clumeck, N. (1984). Acquired immunodeficiency syndrome in Rwanda. Lancet II, 62–65.

Wain Hobson, S., Sonigo, P., Danos, O., Cole, S., and Alizon, M. (1985). Nucleotide sequence of the AIDS virus, LAV. Cell 40, 9–17.

Weiss, R. A. (1984). Human T-cell retroviruses in Molecular Biology of the Tumor Viruses; RNA Tumor Viruses, vol. II, Supplement, R. Weiss, N. Teich, H. Varmus, J. Coffin, eds. (Cold Spring Harbor, New York: Cold Spring Harbor Laboratory), pp. 405–485.

What is claimed is:

1. A human retrovirus, wherein the retrovirus is a mutant of Human Immunodeficiency Virus-1 (HIV-1) which has all the identifying characteristics of HIV-1 OVI, and is in a purified form.

2. An isolate of the human retrovirus of claim 1, wherein the isolate comprises said retrovirus and the retrovirus is capable of being immunologically recognized by human body fluid containing antibodies to the retrovirus.

3. A suspension of the human retrovirus of claim 1 in a buffer therefor, wherein the suspension comprises the human retrovirus, and the human retrovirus is capable of being immunologically recognized by human body fluid containing antibodies to the retrovirus.

4. A human retrovirus, which is retrovirus HIV-1 OYI in a purified form.

5. An immune complex between a human retrovirus as claimed in claim 4, and an antibody specifically recognizing said retrovirus.

6. An immune complex as claimed in claim 5, wherein either component of the complex is labeled with an immunoassay label selected from the group consisting of radioactive, enzymatic, fluorescent, chemiluminescent labels and chromophores.

7. A supernatant of a cell culture infected with a retrovirus as claimed in claim 4, wherein the supernatant comprises the retrovirus in suspension therein.

* * * * *